(12) United States Patent
Hong et al.

(10) Patent No.: US 12,171,549 B2
(45) Date of Patent: Dec. 24, 2024

(54) BLOOD GLUCOSE MEASURING APPARATUS AND OPERATING METHOD OF THE SAME

(71) Applicant: Samsung Electronics Co., Ltd., Suwon-si (KR)

(72) Inventors: Young Jun Hong, Seoul (KR); Jonghan Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 782 days.

(21) Appl. No.: 17/200,100

(22) Filed: Mar. 12, 2021

(65) Prior Publication Data

US 2022/0061709 A1 Mar. 3, 2022

(30) Foreign Application Priority Data

Sep. 1, 2020 (KR) .......................... 10-2020-0111047

(51) Int. Cl.
*A61B 5/145* (2006.01)
*A61B 5/00* (2006.01)

(52) U.S. Cl.
CPC ........ *A61B 5/14532* (2013.01); *A61B 5/0004* (2013.01); *A61B 5/425* (2013.01); *A61B 5/6848* (2013.01); *A61B 5/7221* (2013.01); *A61B 5/7246* (2013.01)

(58) Field of Classification Search
CPC ... A61F 2/022; A61B 5/14532; A61B 5/0031; A61B 5/14546; A61B 5/14865; A61B 5/686
See application file for complete search history.

(56) References Cited

U.S. PATENT DOCUMENTS

| 5,919,216 A | 7/1999 | Houben et al. |
| 6,093,167 A | 7/2000 | Houben et al. |
| 9,962,113 B2 * | 5/2018 | Lang ...................... A61B 5/685 |
| 11,723,558 B2 * | 8/2023 | Papas ................. A61B 5/14539 |
| | | 422/534 |
| 2002/0026141 A1 | 2/2002 | Houben et al. |

(Continued)

FOREIGN PATENT DOCUMENTS

KR 10-1813213 B1 12/2017
WO WO 2011/081596 A1 7/2011

OTHER PUBLICATIONS

Y. Bornat et al., "Detection of Electrical Activity of Pancreatic Beta-cells Using Micro-electrode Arrays," 2010 Fifth IEEE International Symposium on Electronic Design, Test & Applications, Ho Chi Minh City, Vietnam, 2010, pp. 233-236, doi: 10.1109/DELTA.2010.60. (Year: 2010).*

(Continued)

*Primary Examiner* — Eric J Messersmith
(74) *Attorney, Agent, or Firm* — NSIP Law (57) ABSTRACT

A blood glucose measuring apparatus and a method of operating the blood glucose measuring apparatus are provided. The blood glucose measuring apparatus includes a cell capsule comprising a reservoir configured to accommodate cells in a suspension, and an electrode configured to receive electric signals from any one or both of a cell in the suspension that is not in contact with the electrode and a cell in the suspension that is in contact with the electrode, and a cell monitoring device configured to monitor the cells.

24 Claims, 6 Drawing Sheets

(56) References Cited

U.S. PATENT DOCUMENTS

| | | | |
|---|---|---|---|
| 2002/0038083 A1* | 3/2002 | Houben | A61B 5/01 |
| | | | 600/365 |
| 2018/0318566 A1* | 11/2018 | Ferrante | A61M 31/002 |
| 2020/0054257 A1* | 2/2020 | Papas | A61B 5/14532 |

OTHER PUBLICATIONS

Bornat, Yannick, et al., "Detection of electrical activity of pancreatic beta-cells using micro-electrode arrays." *2010 Fifth IEEE International Symposium on Electronic Design, Test & Applications.* IEEE, 2010 (pp. 1-7).

Pfeiffer, Thomas, et al., "Rapid functional evaluation of beta-cells by extracellular recording of membrane potential oscillations with microelectrode arrays." *Pflügers Archiv—European Journal of Physiology*, 462, 6, 2011 (pp. 835-840).

Raoux, Matthieu, et al., "Non-invasive long-term and real-time analysis of endocrine cells on micro-electrode arrays," *The Journal of physiology*, 590, 5, 2012 (pp. 1085-1091).

Nguyen, Quang Vinh, et al., "A novel bioelectronic glucose sensor to process distinct electrical activities of pancreatic beta-cells," *2013 35th Annual International Conference of the IEEE Engineering in Medicine and Biology Society (EMBC). IEEE*, 2013 (pp. 172-175).

Pedraza, Eileen, et al., "Guiding pancreatic beta cells to target electrodes in a whole-cell biosensor for diabetes." *Lab on a Chip*, 15, 19, 2015 (pp. 3880-3890).

Lebreton, Fanny, et al. "Slow potentials encode intercellular coupling and insulin demand in pancreatic beta cells." *Diabetologia*, 58, 6, 2015 (pp. 1291-1299).

\* cited by examiner

FIG. 1

| Cell composition | Cell morphology |
|---|---|
| Pancreatic beta cell | |
| Pancreatic alpha/delta/gamma/epsilon cell | |
| Pancreatic beta cell cluster (>10 cells per cluster) | |
| Pancreatic islet (Pancreatic alpha/delta/gamma/epsilon cell cluster) | |

BLOOD GLUCOSE MEASURING APPARATUS AND OPERATING METHOD OF THE SAME

CROSS-REFERENCE TO RELATED APPLICATIONS

This application claims the benefit under 35 USC § 119(a) of Korean Patent Application No. 10-2020-0111047, filed on Sep. 1, 2020, in the Korean Intellectual Property Office, the entire disclosure of which is incorporated herein by reference for all purposes.

BACKGROUND

Field

The following description relates to a blood glucose measuring apparatus and an operating method of the blood glucose measuring apparatus.

Description of Related Art

A pancreatic islet of a pancreas is a micro-organism containing five types of endocrine cells. Beta cells in pancreatic islets are cells that synthesize, store, and secrete insulin hormone that lowers blood glucose. When blood glucose rises, beta cells secrete stored insulin.

Activity of pancreatic beta cells increases if a glucose concentration in a body increases. For example, membrane potential of beta cells may change in proportion to the glucose concentration, which may be used to detect a concentration of blood glucose in the body.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a blood glucose measuring apparatus including a cell capsule comprising a reservoir configured to accommodate cells in a suspension, and an electrode configured to receive electric signals from any one or both of a cell in the suspension that is not in contact with the electrode and a cell in the suspension that is in contact with the electrode, and a cell monitoring device configured to monitor the cells.

The cells comprise any one of any combination of pancreatic beta cells, a pancreatic beta cell cluster, and a pancreatic islet.

The cell capsule may include a cell reservoir configured to accommodate the cells, a loading port configured to inject one or more cell of the cells into the cell reservoir, a porous membrane configured to enclose an outer boundary of the cell reservoir, and the electrode includes a multi-electrode array (MEA) configured to collect the electric signals generated from the cells.

The MEA may be attached to the porous membrane.

The electrodes of the MEA may be spaced apart from each other and inserted into the porous membrane.

The electrodes of the MEA may be in contact with the cell reservoir by passing through the porous membrane.

The MEA may be located in an internal space of the cell reservoir.

The MEA may have a shape of a needle and may be inserted into the cell reservoir by penetrating the porous membrane.

The cell monitoring device may include an MEA controller configured to control the MEA, a beamformer configured to extract a valid signal based on the electric signals collected by the MEA, and a signal processor configured to estimate a blood glucose concentration based on the valid signal.

The MEA controller may include an amplifier configured to amplify the electric signals, and a switch configured to control a connection between the amplifier and the MEA.

The beamformer may be configured to acquire at least one eigenchannel based on a correlation analysis for the electric signals, to select an eigenchannel from the acquired at least one eigenchannel, and to extract the valid signal based on the selected eigenchannel.

The beamformer may be configured to calculate a cross-covariance matrix for the electric signals and to perform an eigenvalue decomposition on the cross-covariance matrix.

The beamformer may be configured to select at least one of eigenvectors of the cross-covariance matrix based on an order of magnitudes of eigenvalues of the cross-covariance matrix.

The beamformer may be configured to perform a linear transformation of the electric signals based on the selected eigenchannel.

In another general aspect, there is provided a method of operating a blood glucose measuring apparatus, the method includes collecting electric signals generated from cells, at least a portion of the cells being present as a suspension and not being in contact with an electrode within a cell capsule, extracting a valid signal based on the electric signals, and estimating a blood glucose concentration based on the valid signal.

The cells may include any one of any combination of pancreatic beta cells, a pancreatic beta cell cluster, and a pancreatic islet.

The extracting of the valid signal may include acquiring at least one eigenchannel based on a correlation analysis for the electric signals, selecting an eigenchannel from the acquired at least one eigenchannel, and extracting the valid signal based on the selected eigenchannel.

The acquiring of the at least one eigenchannel may include calculating a cross-covariance matrix for the electric signals, and performing an eigenvalue decomposition on the cross-covariance matrix.

The selecting of the eigenchannel may include selecting at least one of eigenvectors of the cross-covariance matrix based on an order of magnitudes of eigenvalues of the cross-covariance matrix.

The extracting of the valid signal may include performing a linear transformation of the electric signals based on the selected eigenchannel.

Other features and aspects will be apparent from the following detailed description, the drawings, and the claims.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Hereinafter, examples will be described in detail with reference to the accompanying drawings. Various modifications may be made to the examples. Here, the examples are not construed as limited to the disclosure and should be understood to include all changes, equivalents, and replacements within the idea and the technical scope of the disclosure.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

When describing the examples with reference to the accompanying drawings, like reference numerals refer to like constituent elements and a repeated description related thereto will be omitted. In the description of examples, detailed description of well-known related structures or functions will be omitted when it is deemed that such description will cause ambiguous interpretation of the present disclosure.

Also, the terms "first," "second," "A," "B," "(a)," "(b)," and the like may be used herein to describe components according to examples. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled, or joined to the second component.

A component having a common function with a component included in one example is described using a like name in another example. Unless otherwise described, description made in one example may be applicable to another example and detailed description within a duplicate range is omitted.

Figure 1:
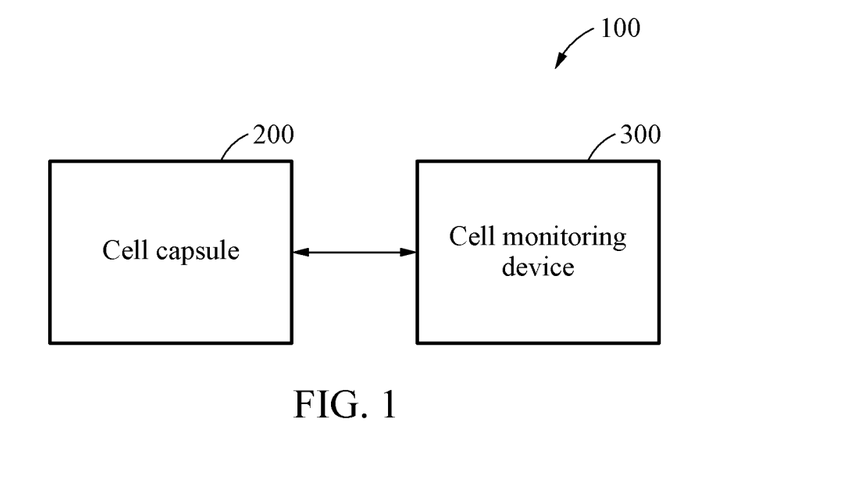
FIG. 1 illustrates an example of a blood glucose measuring apparatus.

FIG. 1 illustrates an example of a blood glucose measuring apparatus 100.

The blood glucose measuring apparatus 100 may measure a blood glucose concentration in a body of a user. For example, the blood glucose measuring apparatus 100 may continue to monitor the blood glucose concentration.

The blood glucose measuring apparatus 100 may measure the blood glucose concentration using cells. For example, the blood glucose measuring apparatus 100 may measure the blood glucose concentration based on a change in a state of a cell that performs an insulin secretion function according to a glucose concentration.

The blood glucose measuring apparatus 100 may measure the blood glucose concentration in an environment in which cells as a suspension are not tightly coupled to an electrode. To measure the blood glucose concentration, the blood glucose measuring apparatus 100 may not require an environment in which cells need to be cultured in an electrode array and are tightly coupled to an electrode.

The blood glucose measuring apparatus 100 may measure the blood glucose concentration in the body in a state of being inserted into the body. The blood glucose measuring apparatus 100 may measure the blood glucose concentration in a condition in which the cells are not tightly coupled to the electrode, and thus it is possible to easily measure the blood glucose concentration even though the blood glucose measuring apparatus 100 is inserted into the body.

The blood glucose measuring apparatus 100 may collect signals generated from a large number of cells and may estimate the blood glucose concentration based on the collected signals. The blood glucose measuring apparatus 100 may enhance a signal-to-noise ratio (SNR) for a valid signal among the collected signals by applying a beamforming algorithm to the collected signals to estimate the blood glucose concentration based on signals (for example, electric signals) generated from the large number of cells.

The blood glucose measuring apparatus 100 may include a cell capsule 200 and a cell monitoring device 300. The blood glucose measuring apparatus 100 may monitor cells accommodated by the cell capsule 200 using the cell monitoring device 300, to measure the blood glucose concentration in the body.

The cell capsule 200 may accommodate cells in a form of a suspension. For example, the cell capsule 200 may provide a space where cells injected from the outside are present as a suspension.

The cell capsule 200 may protect cells in the cell capsule 200 in a state of being inserted into the body. For example, the cell capsule 200 may protect cells from an inflammatory response and/or an immune response in the state of being inserted into the body.

The cell monitoring device 300 may estimate the blood glucose concentration of the user from electric signals collected from the cells in the cell capsule 200. For example, the cell monitoring device 300 may extract a valid signal from the electric signals collected from the cells, and may estimate the blood glucose concentration based on the valid signal.

A configuration and an operation of each of the cell capsule 200 and the cell monitoring device 300 will be further described below.

Figure 2:
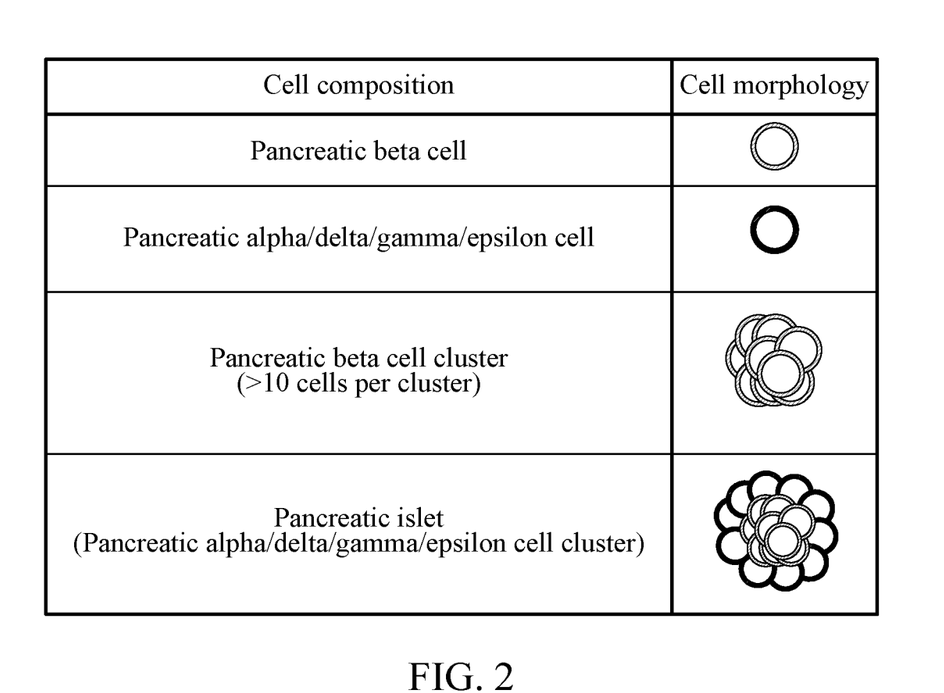
FIG. 2 illustrates an example of cells accommodated by a cell capsule of FIG. 1.

FIG. 2 illustrates an example of cells accommodated by the cell capsule 200 of FIG. 1.

The blood glucose measuring apparatus 100 of FIG. 1 may measure a blood glucose concentration in a body using a cell that performs an insulin secretion function. Cells that perform the insulin secretion function may include, for example, pancreatic beta cells, a pancreatic beta cell cluster, and/or a pancreatic islet.

The cell capsule 200 may accommodate beta cells, a beta cell cluster, and/or a pancreatic islet. However, examples are not limited thereto, and the cell capsule 200 may accommodate various cells that perform the insulin secretion function.

The pancreatic beta cell cluster may be an aggregate including a plurality of pancreatic beta cells. For example, the pancreatic beta cell cluster may be an aggregate in which at least ten pancreatic beta cells are aggregated.

The pancreatic islet may include five types of cells, for example, alpha, beta, delta, gamma, and epsilon cells, associated with an internal secretion. Beta cells among cells in the pancreatic islet may perform a function of perceiving blood glucose in a body and an insulin secretion function.

Since the blood glucose measuring apparatus 100 uses cells that perform the insulin secretion function, the pancreatic islet accommodated by the cell capsule 200 may include pancreatic beta cells and/or pancreatic beta cell clusters that perform the insulin secretion function.

Since a calcium ion (Ca2+) action potential phase and a silent inter-burst phase are repeated based on a variation in an amount of insulin to be secreted and a Ca2+ concentration according to a glucose concentration, membrane potential of pancreatic beta cells may be oscillated with a relatively slow wave.

The blood glucose measuring apparatus 100 may estimate the blood glucose concentration based on an electric signal generated due to a relatively slow wave of membrane potential to cells in the cell capsule 200.

Figure 3:
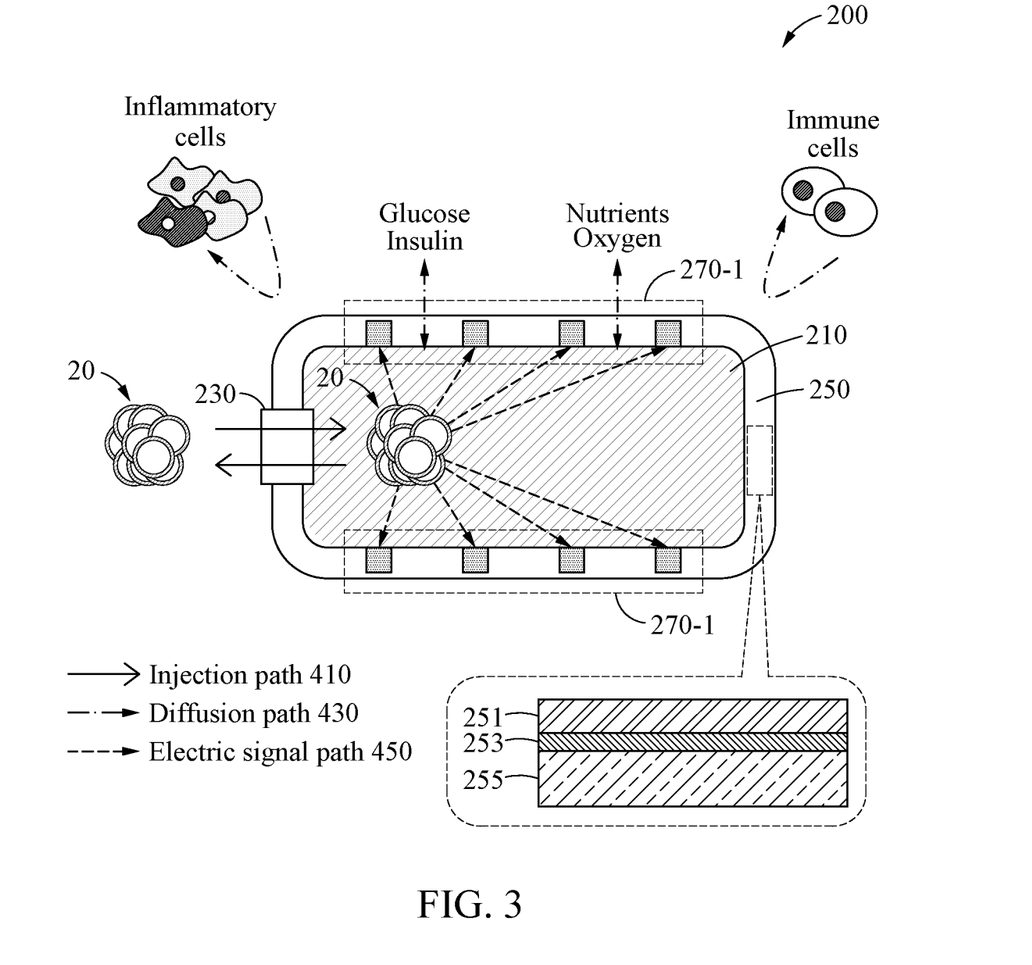
FIG. 3 illustrates an example of the cell capsule of FIG. 1.
Figure 4:
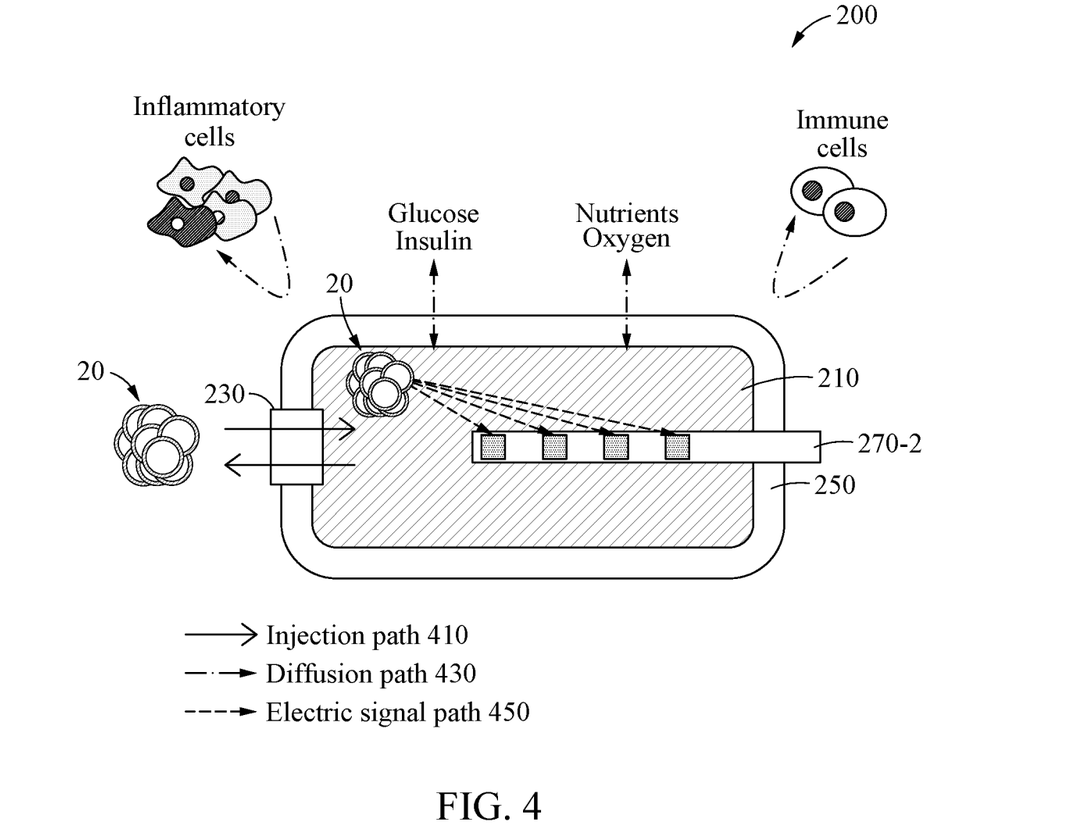
FIG. 4 illustrates another example of the cell capsule FIG. 1.

FIG. 3 illustrates an example of the cell capsule 200 of FIG. 1, and FIG. 4 illustrates another example of the cell capsule 200.

Referring to FIGS. 3 and 4, the cell capsule 200 may include a cell reservoir 210, a loading port 230, a porous membrane 250, and a multi-electrode array (MEA) 270-1 or 270-2. Cells 20 may be cells that perform the insulin secretion function.

The cell reservoir 210 may be a space to accommodate cells 20. For example, the cell reservoir 210 may accommodate the cells 20 that are in a state of a suspension and/or media.

The cells 20 may be injected into the cell reservoir 210 or discharged from the cell reservoir 210, through the loading port 230. Due to a limitation in a lifespan of the cells 20 for an insulin secretion function, cells 20 may be newly injected from the outside through the loading port 230, and cells 20 that reach the end of the lifespan may be discharged to the outside through the loading port 230.

The loading port 230 may connect the cell capsule 200 that is implanted and the outside of the body, so that the cells 20 may be easily injected into the cell reservoir 210 from the outside through the loading port 230 or that the cells 20 may be easily discharged from the cell reservoir 210 to the outside through the loading port 230.

The cell reservoir 210 may be enclosed by the porous membrane 250. For example, cells 20 accommodated in the cell reservoir 210 may be enclosed and accommodated by the porous membrane 250.

The porous membrane 250 may allow body fluids and materials to be selectively exchanged between the inside and the outside of the cell reservoir 210 when the cell capsule 200 is inserted into the body. For example, the porous membrane 250 may allow glucose, insulin, oxygen and/or nutrients to pass therethrough, and may block immune cells and/or inflammatory cells.

Although the porous membrane 250 encloses the entire outer boundary of the cell reservoir 210 as shown in FIGS. 3 and 4, examples are not limited thereto. For example, the porous membrane 250 may enclose a portion of the outer boundary of the cell reservoir 210, and the other portion of the outer boundary may be enclosed by different types of films, covers and/or structures. The above description may also be applicable to an example of FIG. 7.

In an example, the porous membrane 250 may include multiple layers. For example, the porous membrane 250 may include a first membrane layer 251, a second membrane layer 253, and a support fiber layer 255.

The first membrane layer 251 may be disposed adjacent to a cell cluster in the cell reservoir 210. The first membrane layer 251 may prevent immune cells in the body from penetrating the cell reservoir 210. For example, the first membrane layer 251 may be formed of polytetrafluoroethylene, and may have a thickness of about 30 micrometers (μm) and pores with a size less than 0.5 μm.

The second membrane layer 253 may be disposed between the first membrane layer 251 and the support fiber layer 255. For example, the second membrane layer 253 may be formed of polytetrafluoroethylene, and may have a thickness of about 15 μm and pores with a size of about 5 μm.

The support fiber layer 255 may be disposed outside the cell reservoir 210. The support fiber layer 255 may be a layer configured to prevent damages to internal elements due to a physical external force such as a pressure in a body by supporting a mechanical and physical structure. For example, the support fiber layer 255 may be formed of polyester, and may have a thickness exceeding 150 μm and pores with a size exceeding 100 μm.

Due to the above-described structure of the porous membrane 250, glucose, insulin, nutrients and/or oxygen may be free to enter or exit, and an inflow of immune cells and/or inflammatory cells may be blocked. Types and thicknesses of the first membrane layer 251, the second membrane layer 253, and the support fiber layer 255 are not limited to the above description, and may vary depending on a design.

The MEA 270-1 or 270-2 may receive an electric signal generated from a cell 20. The MEA 270-1 or 270-2 may receive electric signals from cells 20 that are present as a suspension in the cell reservoir 210. For example, the MEA 270-1 or 270-2 may receive an electric signal from a cell 20 that is not in contact with an electrode.

The MEA 270-1 or 270-2 may include a plurality of electrodes. The plurality of electrodes may be spaced apart from each other. The plurality of electrodes may collect electric signals generated from cells 20 at different positions. The MEA 270-1 or 270-2 may be located inside and/or outside the cell reservoir 210.

Referring to FIG. 3, the MEA 270-1 may be located in the outer boundary of the cell reservoir 210.

In an example, the MEA 270-1 may be attached to the porous membrane 250. Electrodes of the MEA 270-1 may be spaced apart from each other and may be attached to an inner wall or an outer wall of the porous membrane 250. For example, when an electrode is attached to the outer wall of the porous membrane 250, the electrode may not be in direct contact with the cell reservoir 210. When an electrode is attached to the inner wall of the porous membrane 250, the electrode may be in direct contact with the cell reservoir 210.

In another example, the MEA 270-1 may be inserted into the porous membrane 250. The electrodes of the MEA 270-1 may be spaced apart from each other and may be inserted into a layer of the porous membrane 250. The electrodes inserted into the porous membrane 250 may be in contact with the cell reservoir 210 by passing through the porous membrane 250.

Each of the electrodes of the MEA 270-1 may be located as close as possible to the cell reservoir 210, to easily receive an electric signal from a cell 20.

Referring to FIG. 4, the MEA 270-2 may be located in an internal space of the cell reservoir 210. For example, the MEA 270-2 may have a shape of a needle or a rod, to be inserted into the internal space of the cell reservoir 210 by penetrating the porous membrane 250.

Electrodes of the MEA 270-2 may be spaced apart from each other on a structure with a shape of a needle or a rod. The structure on which the electrodes are disposed may be formed of a soft material.

The cell capsule 200 may perform an intended function through an injection path 410, a diffusion path 430, and an electric signal path 450.

The injection path 410 may be a path along which cells 20 flow into the cell reservoir 210 and/or are discharged from the cell reservoir 210 through the loading port 230. The diffusion path 430 may be a path used to selectively exchange materials, for example, glucose, insulin, oxygen and/or nutrients while performing a function of protecting an inflammatory response and/or immune response in the body through the porous membrane 250. The electric signal path 450 may be a path used to receive electric signals generated from the cells 20 through the MEA 270-1 or 270-2.

Figure 5:
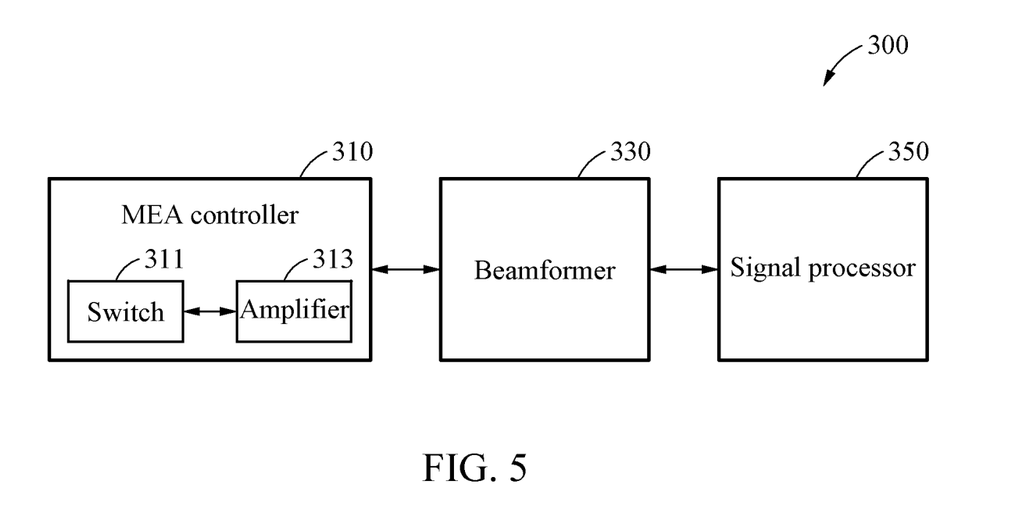
FIG. 5 illustrates an example of a cell monitoring device of FIG. 1.
Figure 6:
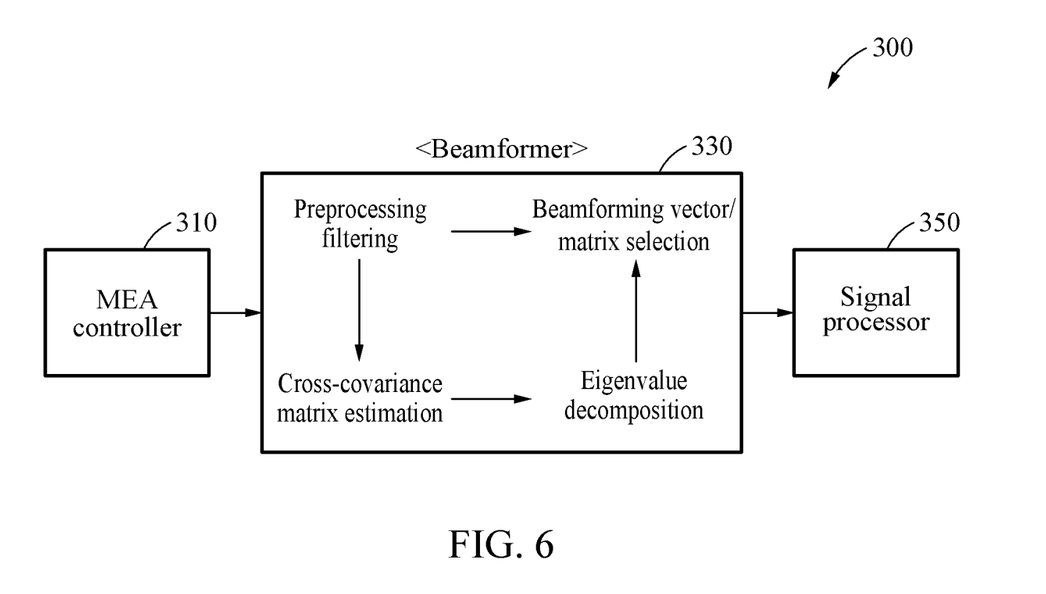
FIG. 6 illustrates an example of an operation of the cell monitoring device of FIG. 1.

FIG. 5 illustrates an example of the cell monitoring device 300 of FIG. 1, and FIG. 6 illustrates an example of an operation of the cell monitoring device 300.

The cell monitoring device 300 may include an MEA controller 310, a beamformer 330, and a signal processor 350.

The MEA controller 310 may control an MEA 270-1 of FIG. 3 or 270-2 or FIG. 4. For example, the MEA controller 310 may control the MEA 270-1 or 270-2 so that signals collected through the MEA 270-1 or 270-2 may be transmitted to the beamformer 330.

The MEA controller 310 may include an amplifier 313 configured to amplify an electric signal, and a switch 311 configured to control a connection between the MEA 270-1 or 270-2 and the amplifier 313.

The beamformer 330 may perform beamforming on electric signals collected through the MEA 270-1 or 270-2. For example, the beamformer 330 may classify a signal space and a noise space of electric signals generated from cells 20 as orthogonal spaces, to enhance a blood glucose estimation performance of the blood glucose measuring apparatus 100.

The beamformer 330 may extract a valid signal by performing a correlation analysis for electric signals. For example, the beamformer 330 may extract a valid signal based on a cross-covariance matrix for electric signals.

The beamformer 330 may perform preprocessing filtering to cancel baseline wander noise, and to acquire a signal within a bandwidth including a target to be measured. For example, the beamformer 330 may cancel the baseline wander noise by performing smoothing using a moving average with a window of 100 milliseconds (ms), and may apply a low-pass filter with a bandwidth of 5 hertz (Hz) to acquire a slow potential frequency generated in cells 20.

A signal x collected through the MEA 270 and received by the beamformer 330 may be represented as shown in Equation 1 below.

$$x(t)=[x_1(t)x_2(t) \ldots x_N(t)]^T \qquad \text{[Equation 1]}$$

The beamformer 330 may enhance the signal x using a beamforming matrix. For example, the beamformer 330 may acquire a valid signal $x_c$ by performing a linear transformation of the signal x based on the beamforming matrix. In this example, the beamforming matrix may include a plurality of beamforming vectors, or may be a beamforming vector as shown in Equation 2 below. When the beamforming matrix is the beamforming vector as shown in Equation 2, the beamformer 330 may acquire the enhanced valid signal $x_c$ as shown in Equation 3 below.

$$w^T=[w_1 w_2 \ldots w_N] \qquad \text{[Equation 2]}$$

$$x_c(t)=x^T \cdot x(t) \qquad \text{[Equation 3]}$$

The beamformer 330 may acquire the beamforming matrix based on a cross-covariance matrix of the signal x. Hereinafter, an example of an operation of the beamformer 330 to derive a beamforming matrix will be described in detail.

The beamformer 330 may calculate the cross-covariance matrix of the signal x. A cross-covariance matrix $K_x$ may be defined as shown in Equation 4 below.

$$K_{x(\tau)} \overset{\Delta}{=} E\left[(x(t)-m_x)(x^T(t+\tau)-m_x^T)\right] = \begin{bmatrix} K_{x_1 x_1}(\tau) & K_{x_1 x_2}(\tau) & \ldots & K_{x_1 x_N}(\tau) \\ K_{x_2 x_1}(\tau) & K_{x_2 x_2}(\tau) & \ldots & K_{x_2 x_N}(\tau) \\ \vdots & \vdots & \ddots & \vdots \\ K_{x_N x_1}(\tau) & K_{x_N x_2}(\tau) & \ldots & K_{x_N x_N}(\tau) \end{bmatrix} \qquad \text{[Equation 4]}$$

In Equation 4, $m_x$ denotes a mean vector of the signal x. The beamformer 330 may calculate the mean vector $m_x$ using Equation 5 shown below.

$$m_x = \begin{bmatrix} m_{x_1} & m_{x_2} & \ldots & m_{x_N} \end{bmatrix}^T \qquad \text{[Equation 5]}$$

$$m_{x_n} = \frac{1}{T}\int_0^T x_n(t)dt$$

The beamformer 330 may calculate a value of each element of the cross-covariance matrix using a cross-covariance function, and each element may be defined as shown in Equation 6 below.

$$K_{x_n x_m}(\tau) = \frac{1}{T} \int_0^T (x_n(t) - m_{x_n})(x_m(t+\tau) - m_{x_m}) dt \quad \text{[Equation 6]}$$

for $n, m = 1, 2, \ldots, N$

The beamformer 330 may perform an eigenvalue decomposition on the cross-covariance matrix. For example, the beamformer 330 may perform the eigenvalue decomposition using a Gaussian elimination or a QR decomposition.

The beamformer 330 may decompose the cross-covariance matrix $K_x$ into a unitary beamforming matrix U including an eigenvector and an eigenvalue matrix $\wedge$ as shown in Equation 7, through the eigenvalue decomposition. The eigenvalue matrix $\wedge$ and the unitary beamforming matrix U may be represented as shown in Equations 8 and 9, respectively. Each element vector, for example, $u_1$ through $u_N$, of the unitary beamforming matrix U may correspond to an eigenchannel.

$$K_x(0) = U \wedge U^T \quad \text{[Equation 7]}$$

$$\wedge = \text{diag}\{\lambda_1, \lambda_2, \ldots, \lambda_N\} \quad \text{[Equation 8]}$$

$$U = [u_1 u_2 \ldots u_N] \quad \text{[Equation 9]}$$

The signal x may be represented based on the unitary beamforming matrix U, as shown in Equation 10 below. A singular value matrix $\Sigma$ and a singular vector $v^T$ may be represented as shown in Equations 11 and 12, respectively.

$$x(t) = U\Sigma v^T(t) \quad \text{[Equation 10]}$$

$$\Sigma = \text{diag}\{\sigma_1, \sigma_2, \ldots, \sigma_N\} \quad \text{[Equation 11]}$$

$$v^T(t) = [v_1(t) v_2(t) \ldots v_N(t)]^T \quad \text{[Equation 12]}$$

When the linear transformation of the signal x is performed based on eigenvectors of the cross-covariance matrix $K_x$, the signal x may be separated into parallel eigenchannels. The beamformer 330 may perform the linear transformation of the signal x based on the unitary beamforming matrix U, and may acquire a size of each of eigenchannels of the signal x. shriek The beamformer 330 may select an eigenchannel of the signal x by selecting at least one of the eigenvectors of the cross-covariance matrix $K_x$. The beamformer 330 may select an eigenvector corresponding to each of eigenvalues of the cross-covariance matrix $K_x$ based on an order of magnitudes of the eigenvalues.

The beamformer 330 may select all eigenchannels, and may utilize a full dimension eigenspace as a signal space. For example, the beamformer 330 may acquire a valid signal $x_c$ based on a beamforming matrix including all eigenvectors. In this example, the valid signal $x_c$ acquired by the beamformer 330 may be represented as shown in Equation 13 below.

$$x_c = [\sigma_1 v_1(t) \sigma_2 v_2(t) \ldots \sigma_N v_N(t)]^T \quad \text{[Equation 13]}$$

The beamformer 330 may select a portion of the eigenchannels, and may utilize a partial dimension eigenspace as a signal space. For example, the beamformer 330 may acquire a valid signal $x_c^n$ based on a beamforming matrix including a portion of the eigenvectors. In this example, the valid signal $x_c^n$ acquired by the beamformer 330 may be represented as shown in Equation 14 below.

$$x_c^n(t) = [\sigma_1 v_1(t) \sigma_2 v_2(t) \ldots \sigma_n v_n(t)]^T \quad \text{[Equation 14]}$$

The beamformer 330 may select a first dominant eigenvector as a beamforming matrix. For example, the beamformer 330 may convert the signal x into a valid signal $x_c$ corresponding to the first dominant eigenchannel. In this example, the valid signal $x_c$ derived by the beamformer 330 may be represented as shown in Equation 15 below.

$$x_c(t) = \sigma_1 v_1(t) \quad \text{[Equation 15]}$$

A signal space cardinality may be determined based on a validity of a strength of an electric signal of a cell 20 collected in the MEA 270. For example, eigenchannels may be selected in connection with a performance of a result of an estimation for a blood glucose concentration of the signal processor 350.

For example, when an algorithm complexity is not considered, the beamformer 330 may utilize the full dimension eigenspace. When the algorithm complexity is considered, the signal space cardinality may adaptively change based on distribution of eigenvalues and/or singular values, or a most dominant eigenchannel may be used.

The beamformer 330 may extract a valid signal by performing the above-described operation in real time. In this example, the beamformer 330 may calculate the cross-covariance matrix $K_x$ every time the beamforming matrix needs to be updated. Due to a relatively high complexity of calculation of the cross-covariance matrix $K_x$, the cross-covariance matrix $K_x$ may be quasi-statically updated based on a coherence time. Also, due to a relatively high complexity of the eigenvalue decomposition to acquire the unitary beamforming matrix U, the beamformer 330 may update the unitary beamforming matrix U based on a degree to which the cross-covariance matrix $K_x$ changes.

An order of eigenchannels derived through beamforming may be determined based on magnitudes of eigenvalues or singular values, as shown in Equations 16 and 17 below. An achievable beamforming gain K may be estimated based on a condition number defined as a ratio between a maximum singular value and a minimum singular value, as shown in Equation 18 below.

$$\lambda_1 \geq \lambda_2 \geq \ldots \geq \lambda_N \quad \text{[Equation 16]}$$

$$\sigma_1 \geq \sigma_2 \geq \ldots \geq \sigma_N \quad \text{[Equation 17]}$$

$$\kappa(x(t)) = \frac{\sigma_{max}(x(t))}{\sigma_{min}(x(t))} \quad \text{[Equation 18]}$$

The signal processor 350 may estimate a blood glucose concentration based on the valid signal extracted by the beamformer 330. The signal processor 350 may estimate the blood glucose concentration based on an electric signal generated due to a slow wave oscillation of membrane potential to cells in the cell capsule 200. In an example, the signal processor 350 may calculate a fraction of plateau phase (FOPP) for the slow wave oscillation of the membrane potential, based on the valid signal, and may estimate the blood glucose concentration. In another example, the signal processor 350 may obtain a frequency of the slow wave oscillation signal by dividing electric signals generated from the cells 20 into action potential and slow potential, based on the valid signal, and may estimate the blood glucose concentration based on the frequency of the slow wave oscillation signal.

The beamformer 330 and the signal processor 350 may each include a processor and a memory, although not shown in the drawings. The processor may execute a computer-readable code, for example, software, stored in the memory and execute instructions induced by the processor.

The term "processor," as used herein, may be a hardware-implemented data processing device having a circuit that is physically structured to execute desired operations. The desired operations may include, for example, code or instructions included in a program.

The hardware-implemented data processing device may include, for example, a microprocessor, a central processing unit (CPU), a processor core, a multi-core processor, a multiprocessor, an application-specific integrated circuit (ASIC), and a field-programmable gate array (FPGA). Further details regarding the processor are provided below.

The memory may store instructions or programs executable by the processor. The instructions may include, for example, instructions to perform an operation of the processor and/or an operation of each component of the processor.

The memory may be implemented as a volatile memory device or a nonvolatile memory device.

The volatile memory device may be implemented as, for example, a dynamic random-access memory (DRAM), a static RAM (SRAM), a thyristor RAM (T-RAM), a zero-capacitor RAM (Z-RAM), or a twin-transistor RAM (TTRAM).

The nonvolatile memory device may be implemented as, for example, an electrically erasable programmable read-only memory (EEPROM), a flash memory, a magnetic RAM (MRAM), a spin-transfer torque (STT)-MRAM, a conductive bridging RAM (CBRAM), a ferroelectric RAM (FeRAM), a phase-change RAM (PRAM), a resistive RAM (RRAM), a nanotube RRAM, a polymer RAM (PoRAM), a nano-floating gate memory (NFGM), a holographic memory, a molecular electronic memory device, or an insulator resistance change memory. Further details regarding the memory are provided below.

The beamformer 330 and the signal processor 350 are separately illustrated in the present disclosure to indicate that the beamformer 330 and the signal processor 350 may be functionally and logically separated, but this does not necessarily imply that the beamformer 330 and the signal processor 350 are realized as physically separate elements or codes.

Figure 7:
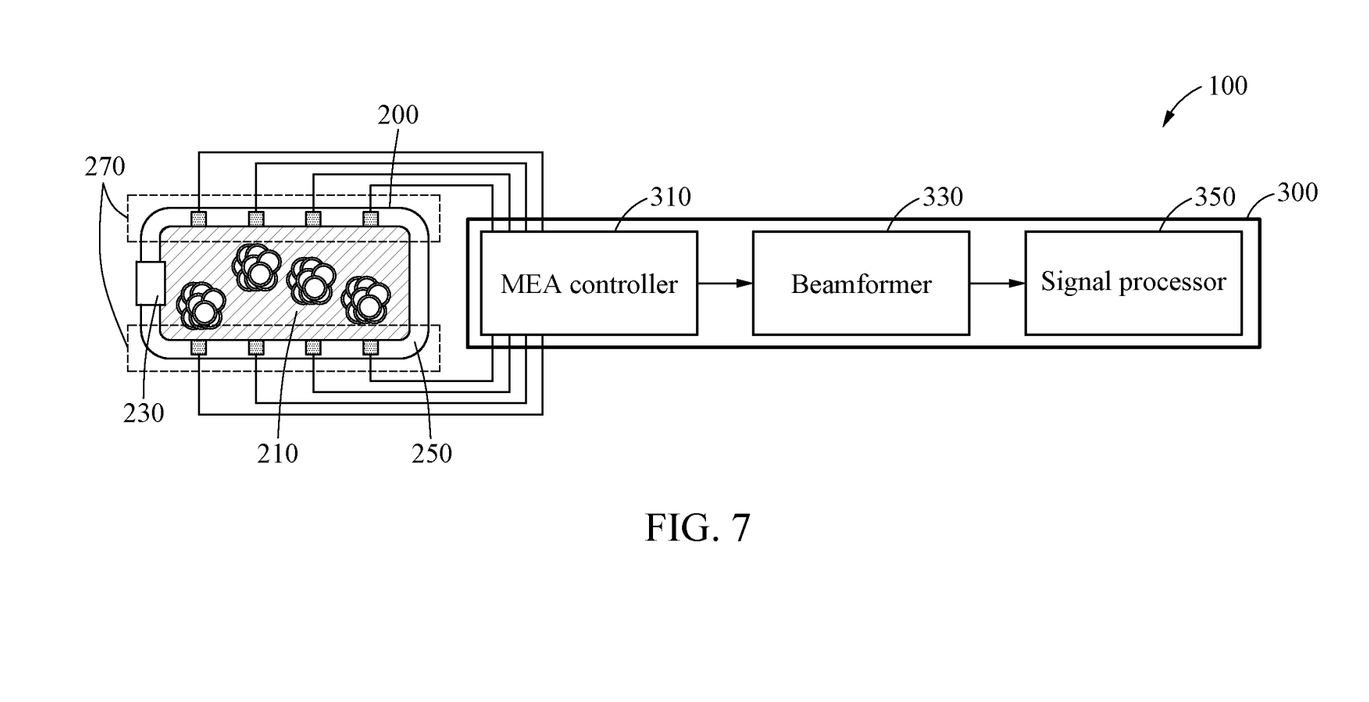
FIG. 7 illustrates an example of relationship between components of the blood glucose measuring apparatus of FIG. 1.
Figure 8:
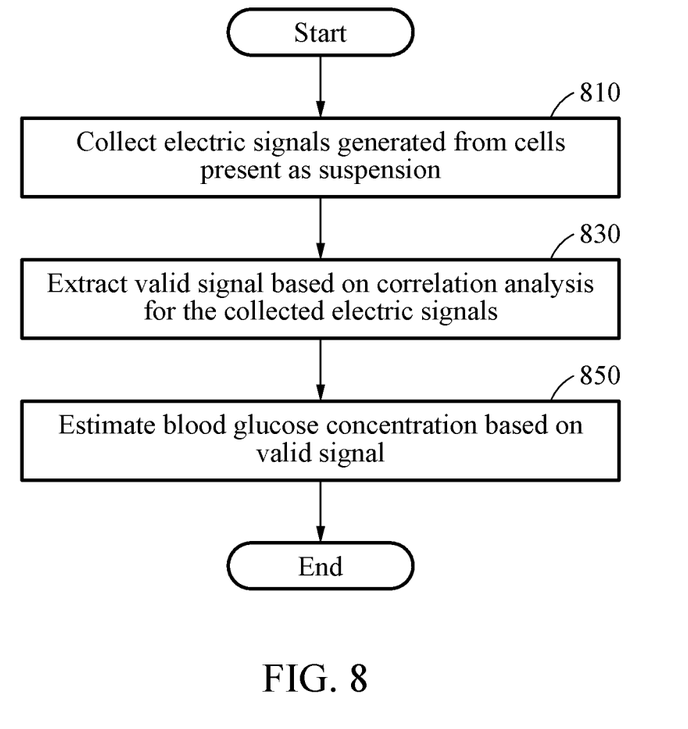
FIG. 8 illustrates an example of an operation of the blood glucose measuring apparatus of FIG. 1.

FIG. 7 illustrates an example of a relationship between components of the blood glucose measuring apparatus 100 of FIG. 1, and FIG. 8 illustrates an example of an operation of the blood glucose measuring apparatus 100. The operations in FIG. 8 may be performed in the sequence and manner as shown, although the order of some operations may be changed or some of the operations omitted without departing from the spirit and scope of the illustrative examples described. Many of the operations shown in FIG. 8 may be performed in parallel or concurrently. One or more blocks of FIG. 8, and combinations of the blocks, can be implemented by special purpose hardware-based computer, such as a processor, that perform the specified functions, or combinations of special purpose hardware and computer instructions, and FIG. 7 illustrates an example of a configuration and an operation of one such apparatus for measuring blood glucose. In addition to the description of FIG. 8 below, the descriptions of FIGS. 1-7 are also applicable to FIG. 8, and are incorporated herein by reference. Thus, the above description may not be repeated here.

In operation 810, the MEA 270 collects electric signals generated from the cells 20 that are present as a suspension. For example, the MEA 270 may collect an electric signal based on a control of the MEA controller 310, and the MEA controller 310 may amplify the electric signal. Although MEA 270 is located in the outer boundary of the cell reservoir 210 as shown in FIG. 7, examples are not limited thereto. For example, the MEA 270 may be located in the internal space of the cell reservoir 210 as shown in FIG. 4. In another example, the MEA 270 may be located in the inner boundary of the cell reservoir 210.

In operation 830, the beamformer 330 extracts a valid signal based on a correlation analysis for the collected electric signals. The beamformer 330 may enhance an SNR for a valid signal among the collected electric signals, and may adjust a cardinality of a signal space, to enhance a reception performance of electric signals generated from the cells 20 that are present as a suspension, and to extract available information from signals generated simultaneously from a large number of cells 20 that are densely concentrated.

In operation 850, the signal processor 350 estimates a blood glucose concentration based on the valid signal. For example, the signal processor 350 may extract a feature associated with the blood glucose concentration from the valid signal, and may estimate the blood glucose concentration.

The cell monitoring device 300, MEA controller 310, beamformer 330, signal processor 350, amplifier 313, and other apparatuses, units, modules, devices, and other components described herein are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, multiple-instruction multiple-data (MIMD) multiprocessing, controller and an arithmetic logic unit (ALU), DSP, microcomputer, field-programmable gate array (FPGA), programmable logic unit (PLU), central processing unit (CPU), graphics processing unit (GPU), neural processing unit (NPU), or any other device capable of responding to and executing instructions in a defined manner.

The methods that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In an example, the instructions or software includes at least one of an applet, a dynamic link library (DLL), middleware, firmware, a device driver, an application program storing the blood glucose measuring method. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), magnetic RAM (MRAM), spin-transfer torque (STT)-MRAM, conductive bridging RAM (CBRAM), ferroelectric RAM (FeRAM), phase-change RAM (PRAM), resistive RAM (RRAM), nanotube RRAM, polymer RAM (PoRAM), nano-floating gate memory (NFGM), holographic memory, molecular electronic memory device, insulator resistance change memory, random-access memory (RAM), dynamic random access memory (DRAM), static random access memory (SRAM), thyristor RAM (T-RAM), zero-capacitor RAM (Z-RAM), twin-transistor RAM (TTRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and providing the instructions or software and any associated data, data files, and data structures to a processor or computer so that the processor or computer can execute the instructions.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A blood glucose measuring apparatus comprising:
   a cell capsule comprising:
      a cell reservoir configured to accommodate cells in a suspension; and
      an electrode configured to, while conductive material of the electrode being not in contact with at least a portion of cells, receive signals generated by the at least portion of the cells; and
   one or more processors configured to generate a glucose measurement signal based on the signals.

2. The apparatus of claim 1, wherein the cells comprise any one of any combination of pancreatic beta cells, a pancreatic beta cell cluster, and a pancreatic islet.

3. The apparatus of claim 1,
   wherein the cell capsule further comprises a loading port configured to inject at least one cell into the cell reservoir, and
   wherein the electrode comprises a multi-electrode array (MEA) configured to collect respective signals generated from multiple cells that have been respectively injected into the cell reservoir by the loading port.

4. The apparatus of claim 3,
   wherein the cell capsule further comprises a porous membrane configured to at least partially enclose an outer boundary of the cell reservoir and prevent immune cells from penetrating, from an exterior of the porous membrane, into the cell reservoir, and wherein the MEA is attached to the porous membrane.

5. The apparatus of claim 3,
wherein the cell capsule further comprises a porous membrane configured to at least partially enclose an outer boundary of the cell reservoir, and
wherein electrodes of the MEA are spaced apart from each other, as disposed in the porous membrane, and respectively contact the cell reservoir.

6. The apparatus of claim 5, wherein the porous membrane is configured to prevent immune cells from penetrating, from an exterior of the cell reservoir, into the cell reservoir.

7. The apparatus of claim 3,
wherein the electrodes of the MEA are disposed along an elongated portion of the MEA that extends away from the porous membrane into the interior space.

8. The apparatus of claim 3, wherein the one or more processors are configured to:
perform a beamforming operation to extract a measurement signal based on the signals; and
estimate a blood glucose concentration based on the measurement signal.

9. The apparatus of claim 8, further comprising a MEA controller that comprises:
an amplifier configured to amplify the signals; and
a switch configured to control a connection between the amplifier and the MEA.

10. The apparatus of claim 8, wherein, for the performance of the beamforming operation, the one or more processors are configured to acquire at least one eigenchannel based on a correlation analysis for the signals, select an eigenchannel from the acquired at least one eigenchannel, and extract the measurement signal based on the selected eigenchannel.

11. The apparatus of claim 10, wherein, for the acquiring of the at least one eigenchannel, the one or more processors are configured to calculate a cross-covariance matrix for the signals, perform an eigenvalue decomposition on the cross-covariance matrix, and determine the at least one eigenchannel based on a result of the eigenvalue decomposition.

12. The apparatus of claim 11, wherein, for the selection of the eigenchannel, the one or more processors are configured to select at least one of eigenvectors of the cross-covariance matrix based on an order of magnitudes of eigenvalues of the cross-covariance matrix to determine the selected eigenchannel.

13. The apparatus of claim 11,
wherein, for the extraction of the measurement signal, the one or more processors are configured to perform a linear transformation of the signals based on the selected eigenchannel, and determine the extracted measurement signal dependent on a result of the linear transformation.

14. The apparatus of claim 2, wherein the electrode and the one or more processors are respectively configured to receive the signals and generate the measurement signal in vivo.

15. The apparatus of claim 7, wherein the porous membrane is configured to prevent immune cells from penetrating, from an exterior of the cell reservoir, into the cell reservoir.

16. The apparatus of claim 8,
wherein the signals of the portion of the cells have respective oscillations that are dependent on a membrane action potential bursts phase and a membrane lower potential inter-burst phase of corresponding cells of the portion of cells,
wherein the extraction of the measurement signal includes distinguishing the signals from noise, and
wherein the estimating of the blood glucose concentration includes considering, based on a result of the extraction, the respective oscillations or differences between the membrane action potential bursts phase and the membrane lower potential inter-burst phase respectively represented in the signals to estimate the blood glucose concentration.

17. A method of operating a blood glucose measuring apparatus, the method comprising:
collecting electric signals generated from cells, at least a portion of the cells being present as a suspension and not being in contact with an electrode within a cell capsule;
extracting a valid signal based on the electric signals; and
estimating a blood glucose concentration based on the valid signal.

18. The method of claim 17, wherein the cells comprise any one of any combination of pancreatic beta cells, a pancreatic beta cell cluster, and a pancreatic islet.

19. The method of claim 17, wherein the extracting of the valid signal comprises:
acquiring at least one eigenchannel based on a correlation analysis for the electric signals;
selecting an eigenchannel from the acquired at least one eigenchannel; and
extracting the valid signal based on the selected eigenchannel.

20. The method of claim 19, wherein the acquiring of the at least one eigenchannel comprises:
calculating a cross-covariance matrix for the electric signals; and
performing an eigenvalue decomposition on the cross-covariance matrix.

21. The method of claim 20, wherein the selecting of the eigenchannel comprises selecting at least one of eigenvectors of the cross-covariance matrix based on an order of magnitudes of eigenvalues of the cross-covariance matrix.

22. The method of claim 19, wherein the extracting of the valid signal comprises performing a linear transformation of the electric signals based on the selected eigenchannel.

23. The method of claim 17,
wherein the collected electric signals of the portion of the cells have respective oscillations that are dependent on a membrane action potential bursts phase and a membrane lower potential inter-burst phase of corresponding cells of the portion of cells,
wherein the extracting of the valid signal includes distinguishing the signals from noise, and
wherein the estimating of the blood glucose concentration includes considering, based on a result of the extracting, the respective oscillations or differences between the membrane action potential bursts phase and the membrane lower potential inter-burst phase respectively represented in the signals to estimate the blood glucose concentration.

24. The method of claim 18, wherein the collecting of the signals and the extraction of the valid signal are performed in vivo.

* * * * *